(12) United States Patent
Koenig et al.

(10) Patent No.: US 8,864,733 B2
(45) Date of Patent: Oct. 21, 2014

(54) FOLDED INCONTINENCE ARTICLE

(75) Inventors: Michael Koenig, Waldstetten (DE);
Hansgeorg Gunesch, Giengen (DE);
Benjamin Wenzel, Garching (DE);
Ruediger Kesselmeier, Herbrechtingen (DE); Christian Koch, Bachhagel (DE)

(73) Assignee: Paul Hartmann AG, Heidenheim (DE)

( * ) Notice: Subject to any disclaimer, the term of this patent is extended or adjusted under 35 U.S.C. 154(b) by 331 days.

(21) Appl. No.: 13/386,905

(22) PCT Filed: Jul. 30, 2010

(86) PCT No.: PCT/EP2010/004677
§ 371 (c)(1),
(2), (4) Date: Mar. 13, 2012

(87) PCT Pub. No.: WO2011/018167
PCT Pub. Date: Feb. 17, 2011

(65) Prior Publication Data
US 2012/0172828 A1    Jul. 5, 2012

(30) Foreign Application Priority Data
Aug. 8, 2009  (DE) .......................... 10 2009 036 796

(51) Int. Cl.
*A61F 13/15*    (2006.01)

(52) U.S. Cl.
USPC ............ 604/385.201; 604/385.16; 604/385.3; 604/385.03; 604/386; 604/396; 604/394

(58) Field of Classification Search
USPC ............. 604/385.201, 385.16, 385.3, 385.01, 604/385.03, 386, 396, 394
See application file for complete search history.

(56) References Cited

U.S. PATENT DOCUMENTS

| | | | |
|---|---|---|---|
| 6,743,213 B1 | 6/2004 | Minato | |
| 2001/0023341 A1 | 9/2001 | Karami | |
| 2002/0123730 A1 | 9/2002 | Popp | |
| 2009/0043275 A1* | 2/2009 | Perneborn | 604/391 |

FOREIGN PATENT DOCUMENTS

| | | |
|---|---|---|
| DE | 10 2004 021 353 | 11/2005 |
| DE | 10 2005 035 544 | 2/2007 |
| EP | 1 005 316 | 6/2000 |
| EP | 1 269 949 | 1/2003 |
| EP | 1 166 735 | 3/2007 |
| JP | 2002-000631 | 1/2002 |
| JP | 2007533383 | 11/2007 |
| WO | WO 2005/102241 | 11/2005 |
| WO | WO 2005/110321 | 11/2005 |
| WO | WO 2007/014623 | 2/2007 |
| WO | WO 2007/058761 | 5/2007 |
| WO | WO 2008/141834 | 11/2008 |

* cited by examiner

*Primary Examiner* — Jacqueline F. Stephens
(74) *Attorney, Agent, or Firm* — Paul Vincent

(57) ABSTRACT

The invention relates to an absorbent open-type incontinence article with attached ears, wherein the rear ears have closure elements in the peripheral region, and to the folding of the ears at high production speeds without the functionality of the closure elements being impaired and with the simultaneously use-friendly arrangement of the closure elements in the folded absorbent incontinence article. The invention also relates to a method of producing this absorbent incontinence article.

12 Claims, 4 Drawing Sheets

FOLDED INCONTINENCE ARTICLE

Figure 1:
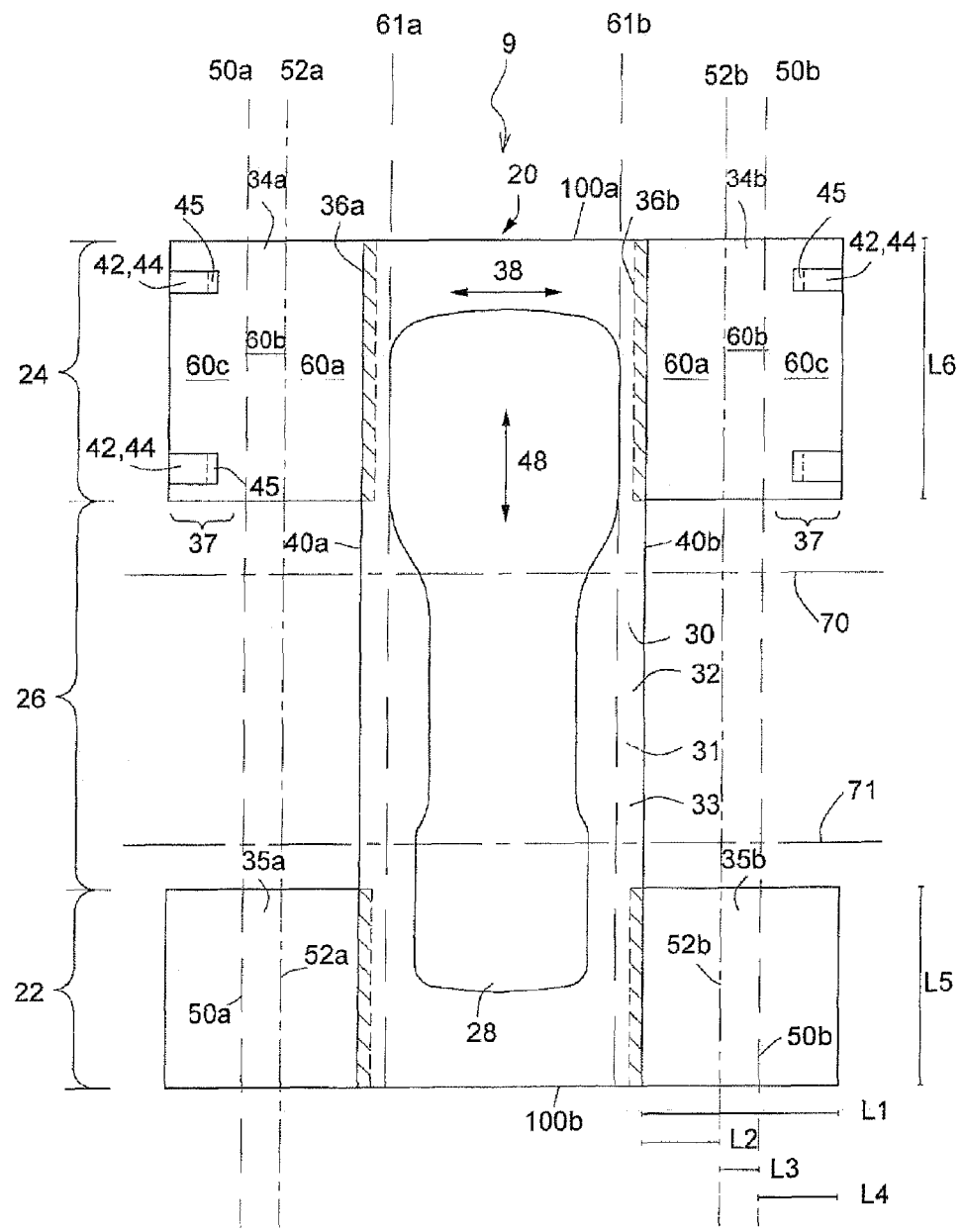

This application is the national stage of PCT/EP2010/004677 filed on Jul. 30, 2010 and claims Paris Convention Priority of DE 10 2009 036 796.9 filed Aug. 8, 2009.

BACKGROUND OF THE INVENTION

The present invention relates to folded, absorbent open-type incontinence articles for incontinent adults, and to a method of folding absorbent incontinence articles.

DE-102005035544-A1 already describes an incontinence article having material portions which are attached to side peripheries of the main part and are often also referred to as ears, which bear closure elements in the peripheral region, wherein the ears are folded onto themselves, and folded in onto that side of the main part which faces the body, about at least two folding lines in order to form an arrangement which has its component parts folded in one above the other and is fixed in a releasable manner at a first point of attachment.

EP-1005316-B1 describes the operation for folding the ears of an open-type diaper in a z-shaped manner and in the case of which in the first instance the outer end of the ears is folded in the rearward direction, by at least the width of the closure surface, and then, in this configuration, is folded back in the forward direction, by double the width of the closure surface, in which case the closure elements in this folded configuration are not concealed by a material layer and are immediately visible to the user.

EP-1166735-B1 likewise describes an operation for folding the rear ears in a z-shaped or inverted-z-shaped manner, wherein initial folding takes place in the inward direction onto the chassis of the diaper and then the free end of the side part is folded over in the outward direction one or more times such that, in the folded state, it is oriented in the outward direction and can easily be unfolded when the diaper has been put on—in particular put onto bedridden individuals.

WO-2005/110321-A1 describes the operation of folding absorbent hygiene articles along first and second longitudinal folding lines such that the outer edges of the ears extend beyond the folding line, in which case the folded article is easy to unfold since the outer edge bearing the closure elements can be reached directly.

WO-2007/058761-A1 describes the production of absorbent hygiene articles with separately attached ears at high machine speeds without the article or the closure elements being inadvertently creased or folded, this being done by folding being carried out which protects the ears and closure elements. For this purpose, the ear, which bears a closure element on its side which is located on the inside when the hygiene article has been placed in position, is folded over onto the inside of the chassis along a longitudinal axis and then the entire side part is folded over onto the chassis along a second longitudinal axis, wherein the second folding width is at least equal to the first, in order that the first inwardly folded region is not folded anew by the second folding operation.

DE-102004021353-A1 discloses an absorbent incontinence article having a main part, made up of a front region, of a rear region and of a crotch region which is located therebetween, as seen in the longitudinal direction, and ends up between a user's legs, wherein the main part comprises an absorbent body, and having rear material portions, which are attached to the rear region, and having front material portions, which are attached to the front region, wherein the rear and front material portions extend in the transverse direction beyond lateral longitudinal peripheries of the main part, wherein the material portions have an inside, which in the use state faces the body, and an outside, which in the use state faces away from the body, and wherein rear material portion, have closure elements on an outer peripheral region of the rear material portions, wherein rear and front material portions connect the front region and the rear region to one another in the use state of the article, and wherein the material portions, prior to initial use of the folded-together article, are folded onto themselves and in the inward direction, onto that side of the rear region of the main part which faces the body.

Proceeding from this prior art, the problem with the folded incontinence articles is that, at high speeds in the production process, the proportion of products produced in a manner which does not conform to specifications increases. Produced in a manner which does not conform to specifications denotes products which do not meet the manufacturer's requirements in respect of product quality. The product quality is impaired as the production speed increases in that the closure elements applied to the folded ears open in an undesired manner during production. If the incontinence article, together with the folded ears and the closure elements which have opened in an undesired manner, is folded longitudinally and/or in the transverse direction in the next production step, then the open, or partially open, closure element comes into contact with other material layers of the incontinence article and is fixed in an undesired manner thereon. As a result, it is no longer possible for the incontinence article to be unfolded in the usual manner and it may be the case that it is no longer possible to use the closure elements for proper fixing. If such an incontinence article were not removed from the production process, then the undesired fixing would become more pronounced upon subsequent packaging of the incontinence article under pressure in a plastics-material bag, in which case such products are unusable since they can no longer be readily opened and put on.

It is an object of the present invention for it to be possible for absorbent open-type incontinence articles with attached ears to be produced at a high production speed without the functionality of the closure means being impaired. The incontinence articles, moreover, should be made available in a user-friendly arrangement.

SUMMARY OF THE INVENTION

This object is achieved according to the invention, in the case of an open-type incontinence article with attached ears (material portions forming side flaps or parts) in that, in a folded arrangement of a rear material portion, the inside of the peripheral region of the material portion is oriented in the direction of that side, of the rear region of the main part which faces the body (that is to say the inside of the rear region of the main part). The lowermost folded sub-portion of the material portion here comprises the peripheral region of the material portion, wherein the peripheral region has closure elements which comprise a closure-element tab which, prior to use, is folded back onto the inside of the material portion, wherein an outer side periphery of the sub-portion projects in the transverse direction by the extent D in relation to the sub-portions folded above the same, that is to say it extends beyond the actual folded formation. The closure-element tabs interact in a releasable adhering manner, for the purpose of closing the incontinence article during use, with an outside of the front region of the main part and/or the material portions in the front region. For this purpose, the closure-element tabs may have, for example, a contact-adhesive zone or mechanical closure aids such as Velcro-type hooks.

The inventors have found that the trigger for the undesired opening of the closure-elements tabs in the production process is a draft-induced force which acts on the closure-elements tabs and increases as the production speed increases. There is a risk of this draft-induced force taking effect, in particular, at the point in time at which the rear material portions in the folded arrangement have already been folded in onto the inside of the main part, and in particular immediately before, or while, the incontinence article is then folded in the transverse direction to its longitudinal direction. If this draft-induced force exceeds the force of adhesion of the closure-element tab on the inside of the material portion onto which it has been folded back, then the closure element opens in an undesired manner. As described above, such incontinence articles are often completely unusable.

The inventors have also found that the closure elements, for the most part, are protected from the air-induced force ocurring in the production process by the arrangement according to the invention. This will be explained in more detail with reference to the figures. Since a lowermost folded sub-portion of the rear material portion comprises the peripheral region of the material portion, and the peripheral region has the closure elements, and an outer side periphery of the sub-portion projects in the transverse direction by the extent D in relation to the sub-portions folded above the same, that is to say it extends beyond the actual folded formation, it is ensured that the user recognizes the rear material portions as such and can conveniently grip and unfold the same.

The extent D here is preferably at least 10%, and at most 90%, of the width of the lowermost sub-portion, further preferably at least 40%, and at most 60%. The projection by the extent D is preferably at least 6 mm and at most 54 mm, further preferably at least 24 mm and at most 36 mm.

The rear material portions, prior to initial use of the folded-together article, are folded onto themselves preferably in zigzag form, preferably along folding lines running parallel to the longitudinal direction, preferably such that the folding lines subdivide the material portions into three sub-portions, the width L3 of the middle sub-portion being smaller than the widths L2 and L4 of the sub-portions adjacent to the middle sub-portion. The ratio of the widths L2, L3 and L4 of the sub-portions is preferably 2:1:2. The folding lines here preferably do not intersect the closure-element tabs folded back onto the inside of the material portions, in which case the width of the outermost sub-portion, which comprises a peripheral region of the respective material portion, corresponds preferably at least to the width of the folded-back closure-element tabs.

Furthermore, it has proven advantageous if a gripping region is present on a respective peripheral region on each of the rear material portions.

In a development of the invention, it has proven advantageous if the rear material portions have a surface-area extent (in cm²) which is greater than that of the front material portions preferably by at least 10%, in particular by at least 15%. In particular the length of the rear material portions, that is to say the extent thereof in the longitudinal direction of the diaper, may be at least 13 cm, further in particular at least 18 cm and furthermore in particular at least 22 cm. It has also proven to be advantageous if the length of the rear material portions is at least 10%, in particular at least 15%, further in particular at least 20%, and furthermore in particular at least 22%, of the overall length of the disposable incontinence article. The overall length of the disposable incontinence article is advantageously 50-120 cm, in particular 60-110 cm and further in particular 70-110 cm. Furthermore, it has proven advantageous if the front material portions have a longitudinal extent which is smaller than that of the rear material portions in particular by at least 5%, further in particular by at least 10%, furthermore in particular by at least 15% and furthermore in particular by at most 50%. In a development of the invention, it has proven advantageous if the width of the material portions, that is to say the extent of the material portions in the transverse direction beyond the side periphery of the main part of the diaper, is 12-40 cm, in particular 13-30 cm, further in particular 14-25 cm. The front material portions are preferably the same width as the rear material portions.

It is advantageously also the case that the front material portions, prior to initial use of the folded-together article, are folded onto themselves preferably in zigzag form, preferably along folding lines running parallel to the longitudinal direction.

It has further proven advantageous to form the front and/or rear material portions from a nonwoven material. Suitable nonwoven materials in particular are all those which contain at least one component based on a thermoplastic polymer. The nonwoven fabrics may contain fibers made of PE, PP, PET, rayon, cellulose, PA and mixtures of these fibers. Fibers with two or more components are also conceivable and advantageous. It is advantageous to use, in particular, card webs, spunbonded nonwovens, hydraulically needled nonwovens, SM nonwovens, SMS nonwovens, SMMS nonwovens or also laminates made of one or more of these types of nonwoven, where S stands for spunbonded nonwoven layers and M stands for meltblown nonwoven layers. It is particularly preferred to use spunbonded nonwovens, since these have a high strength in the longitudinal and transverse directions and can thus withstand to particularly good effect the shearing forces acting on them as a result of the engagement of mechanical closure aids which may be present. In order to prevent fibers from being torn out of the nonwoven composite when the mechanical closure aids are released, it is advantageous for the nonwoven-fabric component to be provided with an embossed design, by means of which preferably all the fibers of the nonwoven component are bonded. It is advantageous in such a case to use, in particular, a thermally embossed design, which is generated in particular advantageously by calendering the nonwoven fabric, heat energy being supplied in the process.

For the purpose of producing a folded incontinence article according to the invention, the rear material portions are folded onto themselves in zigzag form preferably along at least two folding lines parallel in the longitudinal direction, and the folded material portions are folded in in the inward direction onto that side of the rear region of the main part of the diaper which faces the body, along folding-in axes running preferably through the main part. It would advantageously also be possible for the side periphery of the main part to form the folding-in axes in the region of attachment of the rear material portions.

Accordingly, the invention also relates to a method of producing a folded incontinence article as claimed, wherein the rear material portions are folded onto themselves preferably in zigzag form along folding lines parallel in the longitudinal direction, and the folded rear material portions are folded-in in the inward direction onto that side of the rear region of the main part which faces the body, along the folding-in axes, such that the inside of the peripheral region of a respective rear material portion is oriented in the direction of the side facing the body, that is to say the inside of the rear region of the main part. The material portions are preferably in the first instance folded onto themselves and then folded in onto the rear region of the main part. It is also preferable for the material portions first of all to be folded onto themselves, then to be fixed, in the folded configuration, on the rear region of the main part and then folded in onto the inside of the main part.

In a development of this idea of the invention, the incontinence article is folded onto itself at least once, preferably twice, in the inward direction, preferably along folding lines running in the transverse direction, preferably such that in the first instance the front region is folded in the inward direction onto the inside of the main part and then the rear region is folded onto the front region. This gives rise to a product which is easy to handle in the production and packaging processes on account of its compact size and of which the visible sides, in the folded-together configuration, are formed by the material layer which also forms the outermost layer in the use state, in which case the inside of the article is protected against contamination prior to use.

The incontinence articles are preferably conveyed during production in a production machine, in particular following the method step of zigzag folding and of folding in the rear material portions in the inward direction onto that side of the rear region of the main part which faces the body, along the folding-in axes, parallel to the longitudinal direction and at a web speed of more than 200 m/min, in particular more than 250 m/min, further in particular of more than 300 m/min, and furthermore in particular of more than 350 m/min. The incontinence articles here, up to and including this aforementioned method step, are preferably still conveyed in an endless state, that is to say still with their respective later hip-opening peripheries connected to one another. It is preferably only in a subsequent method step that the incontinence articles are separated from one another in the transverse direction to form the separated incontinence articles, and are then, as described above, folded onto themselves along folding lines running in the transverse direction.

BRIEF DESCRITION OF THE DRAWNING

Figure 2:
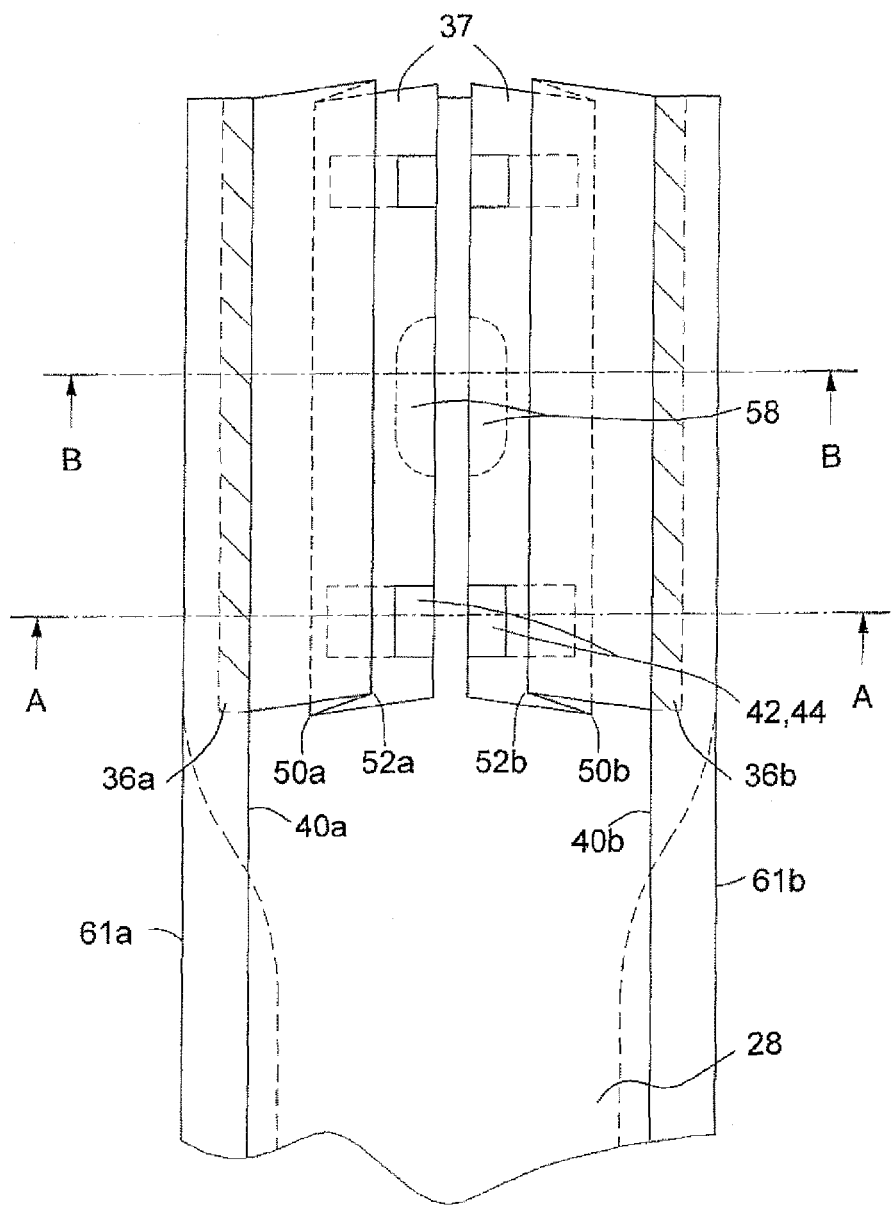
Figure 2A:
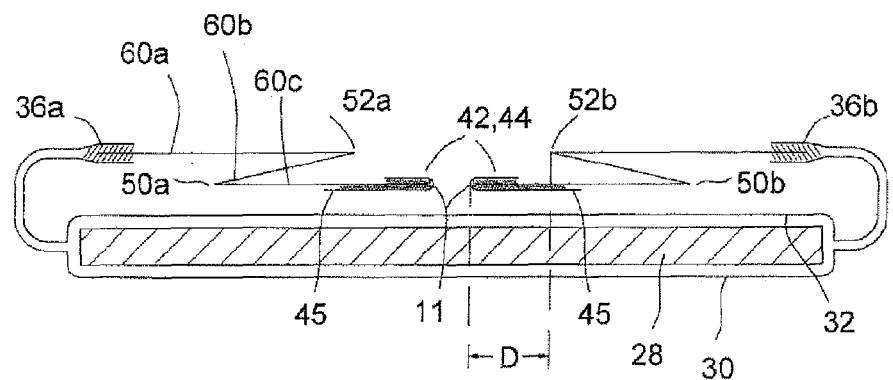
Figure 2B:
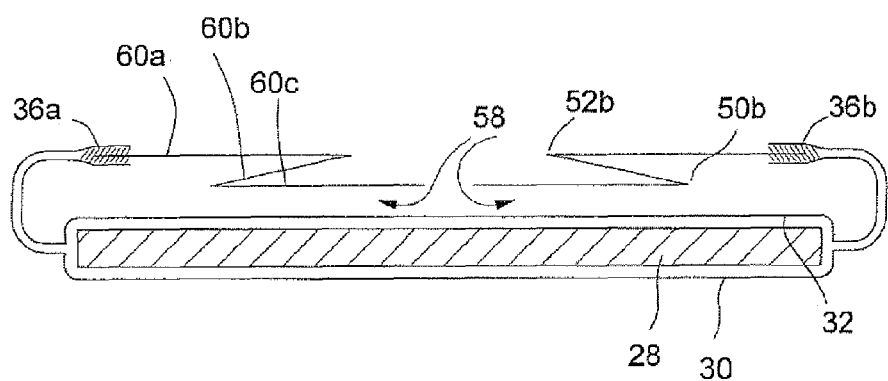
Figure 2C:
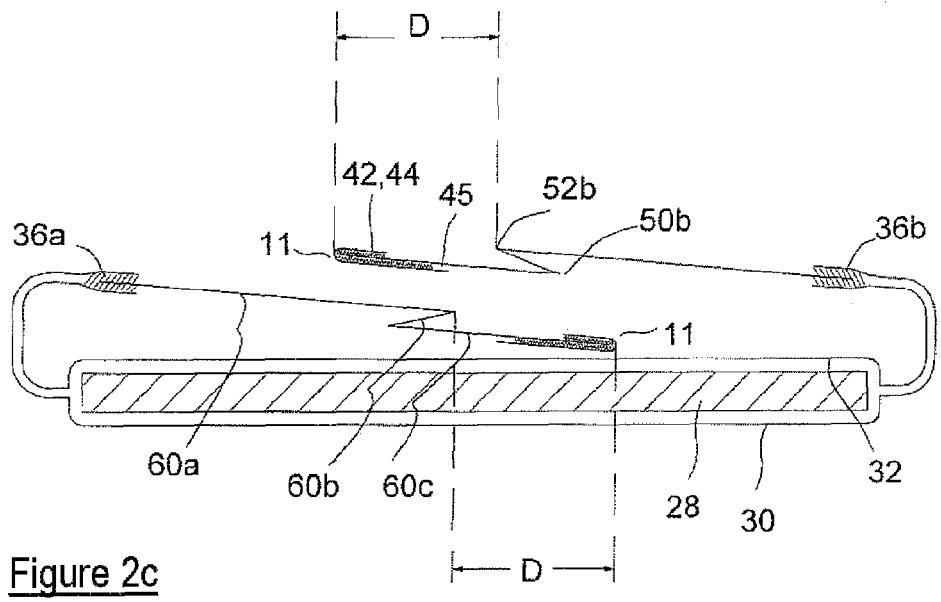
Figure 3A:
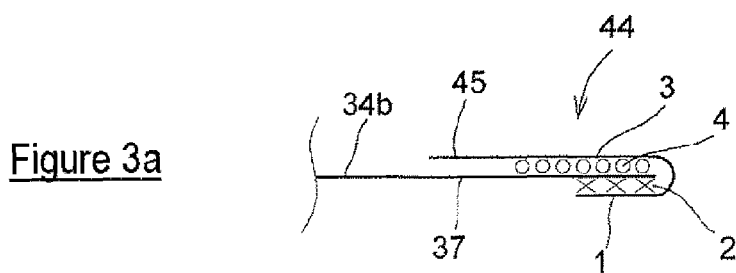
Figure 3B:
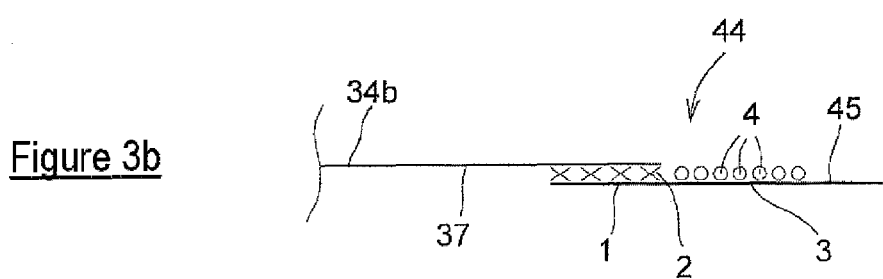

Further features, details and advantages of the invention can be gathered from the accompanying patent claims, from the illustrations and from the following description of the preferred embodiment of the invention. In the drawings:

FIG. 1 shows a plan view of a fully unfolded incontinence article,

FIG. 2 shows a plan view of part of an incontinence article folded according to the invention, and having rear material portions folded onto themselves, FIG. 2a shows a sectional view of the incontinence article according to FIG. 2(A-A), FIG. 2b shows a sectional view of the incontinence article according to FIG. 2(B-B), FIG. 2c shows a sectional view of the incontinence article according to FIG. 2 (A-A) in an alternative embodiment, and FIGS. 3a and 3b show sectional views of a closure element attached to the peripheral region of a rear material portion.

DESCRITION OF THE PREFERRED EMBODIMENT

An incontinence article 9 according to the invention is illustrated schematically in FIGS. 1 to 2b. It comprises a main part, which is designated as a whole by reference sign 20 and is often also referred to as a chassis. The main part 20 comprises a front region 22, a rear region 24 and a crotch region 26, which is located therebetween and ends up between a user's legs when the incontinence article 9 is put onto a user. The main part 20 comprises an absorbent body 28, which is suitably dimensioned for absorbing, and permanently storing, bodily fluids. The absorbent body preferably comprises cellulose fibers and super-absorbent polymer particles (SAP) and has a liquid-impermeable layer 30 running beneath it, it also being possible for this layer 30 to form the outermost, visible side of the incontinence article 9. A liquid-permeable top sheet 32 may be provided above the absorbent body 28.

In the rear region 24, a first material portion 34a, which forms a rear side flap or side portion, is attached to a first side-periphery portion 36a of the main part 20 and a second material portion 34b, which forms a rear side flap or side portion, is attached to a second side-periphery portion 36b of the main part 20. The material portions 34a, 34b have a rectangular contour. It would also be conceivable, and advantageous, to have material portions 34a, 34b which are contoured at the leg cutout, as disclosed in DE 102007024180-A1. The outer transverse peripheries of the main part 20 and the rear material portions 34a, 34b form the rear hip-opening periphery 100a.

That side of the incontinence article 9 which in the use state faces away from the wearer's body, is referred to as outside 31, and that side of the incontinence article 9 which in the use state faces the wearer's body is referred to as inside 33. By this understanding, with the incontinence article 9 in the folded-out-flat configuration, each component of the incontinence article 9 can be assigned an inside and an outside.

FIG. 1 shows a view of the inside 33 of the incontinence article 9 in the fully unfolded state. The rear material portions 34a, 34b each bear two closure elements 42 with closure-element tabs 44 which are folded onto themselves, can be unfolded for intended use and have free finger lifts 45. The closure-element tabs 44 interact in a releasably adhering manner, for the purpose of closing the incontinence article during use, with an outside 31 of the front region 22 of the main part 20 and/or the material portions in the front region 22. For this purpose, the closure-element tabs may have a contact-adhesive zone or a zone with mechanical closure aids such as Velcro-type hooks.

The front region 22 of the incontinence article likewise has material portions 35a, 35b which are folded onto themselves and form side portions, but these do not have any closure elements. The front material portions 35a, 35b have a rectangular contour. It would also be conceivable, and advantageous, to have material portions 35a, 35b which are contoured at the leg cutout, as disclosed in DE 102007024180-A1. The outer transverse peripheries of the main part 20 and the front material portions 35a, 35b form the front hip-opening periphery 100b.

The respective rear material portion 34a, 34b in the rear region 24 of the main part, as can be seen from FIG. 2a, is folded onto itself in zigzag form along in each case two folding lines 50a, 52a and 50b, 52b, respectively, parallel in the longitudinal direction 48, wherein sub-portions 60a, 60b, 60c of a material portion end up located one upon the other in certain regions.

During production of the incontinence articles 9, the respective rear material portions 34a, 34b, starting from the illustration according to FIG. 1 and after they have been folded onto themselves in zigzag form, are folded over in the inward direction along respective folding-in axes 61a, 61b, which are parallel to the longitudinal direction 48 and in the embodiment illustrated run within the main part 20, into the position which is illustrated in FIG. 2, to give a folded-in arrangement. In this arrangement, the incontinence articles 9, during production, are conveyed in particular still in the endless state in the longitudinal direction at a high web speed, in particular at a web speed of more than 200 m/min, further in particular at a web speed of more than 300 m/min, furthermore in particular at a web speed of more than 350 m/min. In such a case, the upper side of the web is subjected to a pronounced draft ("relative wind"). This has the risk of the components which form the upper side of the web being subjected to pronounced draft-induced force. Since an outer side periphery 11 of the lowermost sub-portion 60c of a rear material portion 34a or 34b projects in the transverse direction by the extent D in relation to the sub-portions 60a and 60b folded above the same, at least one sub-region of a lowermost sub-portion 60c at least of a rear material portion forms a sub-region of the upper side of the web. The inventors have found that, in this configuration, the closure-element tabs are exposed, to a particular extent, to the risk of the action of pronounced draft-induced forces leading to production errors: the closure-element tab 44 has its production end 1 fixed usually in a non-releasable manner, that is to say very securely, on a peripheral region 37 of the rear material portions 34a, 34b (FIG. 3a) preferably by means of a permanent adhesive 2 or else by means of thermobonding or ultrasonic welding or other attachment methods. At its user end 3, in contrast, the closure-element tab 44 is usually fixed such that it can be detached, without being destroyed, for the purpose of later use, that is to say such that it can be unfolded into the use state by the user applying only a small amount of force, fixing here taking place preferably by means of a contact adhesive 4 and/or by means of mechanical closure elements such as Velcro-type hooks. FIG. 3b shows the closure-element tab 44 unfolded as intended, immediately prior to use of the incontinence article, following its detachment, without being destroyed, from the inside 33 of the peripheral region 37 of a rear material portion 34a, 34b. Moreover, the closure-element tab 44 has, at an outmost region of its user end 3, a so-called finger lift 45, that is to say an end portion which, for the purpose of being gripped straightforwardly by the user, can be detached with an even smaller amount of force being applied, or preferably, as in the case illustrated, remains unfixed altogether.

In the arrangement according to the invention, it is ensured that, in the folded arrangement, the detachable user end 3 of the closure-element tab 44, together with the finger lift 45 thereof, is oriented in the direction of the side facing the body, that is to say of the inside 33 of the rear region 24, that is to say faces this inside, and is thus not part of the upperside of the web and is therefore exposed to the abovedescribed draft-induced forces to a less pronounced extent, if at all. Instead, the production end 1, which is fixed permanently, that is to say in a non-releasable manner, is part of the upperside of the web. It is thus the case that the production end 1 is exposed to the draft-induced forces to a more pronounced extent, but it can withstand the same to better effect since it is intentionally fixed on the peripheral region 37 of the rear material portion 34a, 34b in a non-releasable manner, that is to say with a considerably more pronounced force of adhesion. The arrangement according to the invention also ensures that the user recognizes the rear material portions 34a, 34b as such, that is to say can distinguish them from the front side portions and, moreover, can conveniently grip and unfold the same since a lowermost folded sub-portion 60c of the rear material portion 34a, 34b comprises the peripheral region 37 of the material portion, and the peripheral region 37 has the closure elements 44, and an outer side periphery 11 of the sub-portion 60c projects in the transverse direction 38 by the extent D in relation to the sub-portions 60a, 60b folded above the same, that is to say it extends beyond the actual folded formation.

Furthermore, it has proven advantageous if a gripping region 58 is present on a respective peripheral region on each of the rear material portions 34a, 34b (FIG. 2b). The gripping region 58 is the region which is suitable for gripping the folded material portion 34a, 34b manually in order to unfold the same. The respective gripping region 58 of the material portions 34a, 34b, in the configuration illustrated in FIG. 2, faces inward in the direction of a longitudinal center axis of the incontinence article 9.

Further preferably, a respective rear material portion 34a, 34b is folded such that an outer side periphery 11 of the lowermost sub-portion 60c of a rear material portion 34a, 34b projects by the extent D in the transverse direction in relation to the sub-portions 60a, 60b folded thereabove, and is thus easier for the user to grip. D here is preferably at least 10%, and at most 90%, of the width L4 of the sub-portion 60c, further preferably at least 40%, and at most 60%. The projection by the extent D is preferably at least 6 mm and at most 54 mm, further preferably at least 24 mm and at most 36 mm.

In a preferred embodiment, the sub-portions 60a, 60b, 60c of the material portions 34a, 34b folded one upon the other are fixed preferably in a releasable manner in this folded configuration in particular by punctiform points of attachment 62 produced by ultrasonic welding, preferably having a diameter of 0.35 m and a surface area of 0.0962 $mm^2$, these being illustrated in FIG. 2. It has been found that this releasable fixing may be configured such that the respective material portion 34a, 34b can be unfolded to the full extent by the respective first gripping region 58 being pulled once, wherein preferably all the points of attachment 62 are released or undone.

In the preferred embodiment illustrated, the rear material portions 34a, 34b folded one upon the other in the longitudinal direction are folded in onto the inside of the rear region 24, along the folding-in axes 61a, 61b, such that the material portions 34a, 34b end up in abutment, or at a small spacing apart from one another, but not overlapping one another (FIG. 2a).

However, in an alternative embodiment, it is conceivable and advantageous for the rear material portions 34a, 34b folded one upon the other in the longitudinal direction to be folded in onto the inside of the rear region 24, along the folding-in axes 61a, 61b, to such an extent that the material portions 34a, 34b end up overlapping one another at least in certain regions (FIG. 2c).

Once the rear and front material portions have been folded longitudinally, and the folded material portions have been folded in onto the inside of the main part, the incontinence article 9 is folded onto itself preferably at least once, preferably twice, in the inward direction, preferably along folding lines 70, 71 running in the transverse direction 38 (FIG. 1), preferably such that in the first instance the front region 22 is folded in the inward direction onto the inside 33 of the main part 20 and then the rear region 24 is folded onto the front region 22. This gives rise to a product which is easy to handle in the production and packaging processes on account of its compact size and of which the visible sides, in the folded-together configuration, are formed by the material layer 30 which also forms the outermost layer in the use state, in which case the inside 33 of the article 9 is protected against contamination prior to use.

FIG. 1 depicts the dimensions of the sub-portions 60a, 60b, 60c of the respective material portion in the embodiment illustrated. The overall extent L1 in the transverse direction 38 of a front and rear material portion in the unfolded state is 165 mm. The width L2 of the sub-portion 60a which is adjacent to the main part 20, is approximately 70 mm. The width L3 of the middle sub-portion 60b is approximately 35 mm, and the width L4 of the outer sub-portion 60c, which comprises the peripheral region 37, is approximately 60 mm.

The length of the material portions in the front region L5 is 165 mm, and the length of the material portions in the rear region L6 is 230 mm.

We claim:

1. An absorbent incontinence article, the article comprising:
a main part having a front region, a rear region and a crotch region disposed, as seen in a longitudinal direction, between said front region and said rear region for positioning between legs of a user, said main part also having an absorbent body; rear material portions attached to said rear region; front material portions attached to said front region, said rear and front material portions extending in a transverse direction beyond lateral longitudinal peripheries of said main part, wherein said rear and front material portions connect said front region and said rear region to one another in a use state of the article, said rear and front material portions having an inside, which, in the use state, faces a body of the user and an outside, which in the use state, faces away from the body; and closure elements disposed at said rear material portions on an outer peripheral region thereof, each of said closure elements having a closure element tab with a free finger lift, said closure element tab being inseparably joined with a first end thereof to said outer peripheral region of said rear material portion and extending, in an unfolded state, in the transverse direction beyond said outer peripheral region of said rear material portion, said closure element tab being folded back onto said inside of said rear material portion prior to use of the article, wherein said closure element tab has a region which is releasable adhered to said inside of said rear material portion using adhesive and/or a mechanical closure means such as hooks, said free finger lift being an end section of said closure element tab which is not joined to said inside of said rear material portion, thereby facilitating simplified gripping thereof by the user, wherein, prior to initial use of the article, said rear material portions are folded onto themselves in zigzag form and are subsequently folded in a transverse, inward direction onto a side of said rear region of said main part which faces the body, thereby creating a folded arrangement along folding lines running parallel to said longitudinal direction, said folding lines subdividing said rear material portions into sub-portions, wherein, in a folded arrangement of the article, a lowermost
folded sub-portion of said material portions comprises said outer peripheral region, an inside of said outer peripheral region being oriented towards said side of said rear region of said main part which faces the body, wherein a respective rear material portion is folded such that an outer side edge of said lowermost folded sub-portion of said rear material portion projects in said transverse direction by an extent D relative to sub-portions folded above the same.

2. The absorbent incontinence article of claim 1, wherein said extent D is at least 10% and at most 90% or at least 40% and at most 60% of a width of said lowermost folded sub-portion.

3. The absorbent incontinence article of claim 1, wherein a projection by said extent D is at least 6 mm and at most 54 mm or at least 24 mm and at most 36 mm.

4. The absorbent incontinence article of claim 1, wherein said folding lines subdivide said rear material portions into three sub-portions, wherein a width of a middle sub-portion is smaller than widths of sub-portions adjacent to said middle sub-portion.

5. The absorbent incontinence article of claim 4, wherein a ratio of widths of said three sub-portions is 2:1:2.

6. The absorbent incontinence article of claim 1, wherein a gripping region is structured on said outer peripheral region of each of said rear material portions.

7. The absorbent incontinence article of claim 1, wherein said rear material portions, folded one upon an other in said longitudinal direction, are folded in onto an inside of said rear region along folding-in axes, such that said front and said rear material portions overlap one another, partially overlap one another, are in abutment or are at a small spacing apart from one another.

8. The absorbent incontinence article of claim 1, wherein, prior to initial use of a folded-together article, said front material portions are folded onto themselves along folding lines running parallel to said longitudinal direction.

9. The absorbent incontinence article of claim 1, wherein, prior to initial use of a folded-together article, said front material portions are folded onto themselves in zigzag form along folding lines running parallel to said longitudinal direction, said folding lines subdividing said front material portions into three sub-portions having a ratio of widths of said three sub-portions of 2:1:2.

10. A method for producing the incontinence article of claim 1, wherein the rear material portions are folded onto themselves in zigzag form along folding lines parallel to the longitudinal direction, folded rear material portions being folded along folding-in axes in an inward direction onto a side of the rear region of the main part which faces the body such that an inside of the peripheral region of a respective rear material portion is oriented towards an inside of the rear region of the main part.

11. The method of claim 10, wherein incontinence articles are conveyed in a production machine, parallel to the longitudinal direction, at a web speed of more than 200 m/min, of more than 250 m/min, of more than 300 m/min or of more than 350 m/min.

12. The method of claim 10, wherein incontinence articles are folded onto themselves at least once or twice, in an inward direction or along folding lines running in the transverse direction such that the front region is first folded onto an inside of the main part and the rear region is then folded onto an outside of the front region.

* * * * *